United States Patent [19]

Meyer et al.

[11] 4,318,994

[45] Mar. 9, 1982

[54] ENTEROBACTERIACEAE SPECIES BIOCHEMICAL TEST CARD

[75] Inventors: Michael C. Meyer, Hazelwood; Leodis V. Woods, St. Louis; James J. Underwood, Ballwin; Ralph Wilkinson, Florissant, all of Mo.; Victoria Stratman, Galesburg, Ill.

[73] Assignee: McDonnell Douglas Corporation, Long Beach, Calif.

[21] Appl. No.: 238,682

[22] Filed: Feb. 26, 1981

Related U.S. Application Data

[63] Continuation of Ser. No. 70,964, Aug. 30, 1979, abandoned.

[51] Int. Cl.³ .................... C12M 1/20; C12M 1/34
[52] U.S. Cl. ............................ 435/301; 435/33; 435/34; 435/291; 435/808
[58] Field of Search ............ 435/32, 33, 34, 35, 435/36, 37, 38, 287, 288, 291, 299, 300, 301, 805, 808, 810; 422/58, 61; 356/244, 246

[56] References Cited

U.S. PATENT DOCUMENTS

| | | | |
|---|---|---|---|
| 3,018,611 | 1/1962 | Biritz | 422/58 |
| 3,370,175 | 2/1968 | Jordon | 435/32 |
| 3,784,448 | 1/1974 | Cekoric | 435/38 |
| 3,799,742 | 3/1974 | Coleman | 422/61 |
| 3,919,053 | 11/1975 | Nazemi | 435/291 |
| 3,957,583 | 5/1976 | Gibson | 435/38 |
| 4,018,652 | 4/1977 | Landam | 435/38 |
| 4,038,151 | 7/1977 | Fadler | 435/33 |
| 4,077,845 | 3/1978 | Johnson | 435/33 |
| 4,116,775 | 9/1978 | Charles | 435/291 |

Primary Examiner—Ernest G. Therkorn
Attorney, Agent, or Firm—George W. Finch; Donald L. Royer; John P. Scholl

[57] ABSTRACT

An improved card for use in an automated machine to detect the continued existence of microbes in a plurality of wells containing different media so that the organism can be speciated. The card includes an improved configuration wherein the wells have different reduced oxygen environments and all of the wells have an improved bubble chamber connected to the well by a bifurcated passage.

13 Claims, 4 Drawing Figures

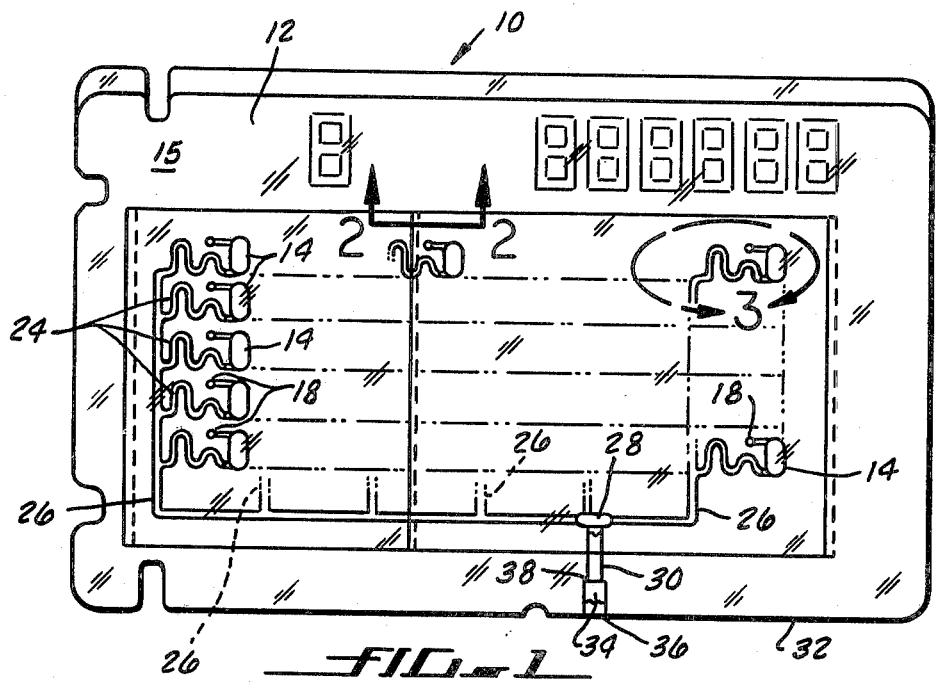
FIG.—1
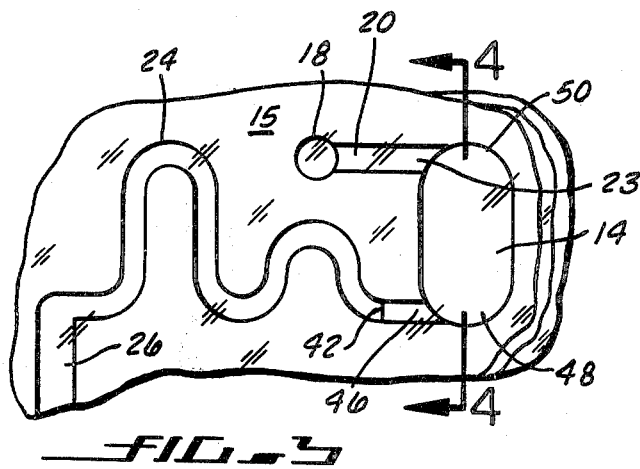
FIG.—3
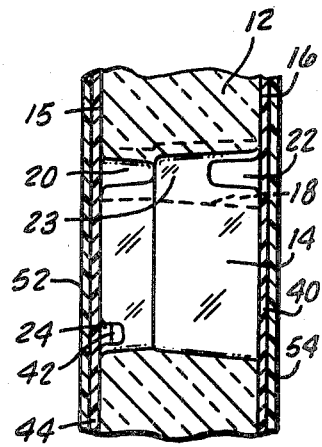
FIG.—4
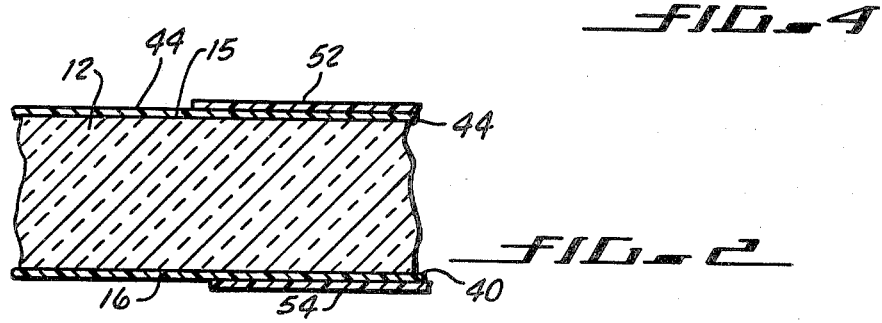
FIG.—2

ENTEROBACTERIACEAE SPECIES BIOCHEMICAL TEST CARD

This is a continuation of patent application Ser. No. 70,964, filed Aug. 30, 1979, now abandoned.

CROSS REFERENCE TO RELATED PATENTS

This application discloses an improved card similar to those shown in: U.S. Pat. No. 4,018,652 entitled "Process and Apparatus for Ascertaining the Concentration of Microorganisms in a Water Specimen" by J. W. Lanham, et al; U.S. Pat. No. 3,957,583 entitled "Apparatus and Process for Determining the Susceptibility of Microorganisms to Antibiotics" by S. F. Gibson, et al; U.S. Pat. No. 4,038,151, entitled "Card For Use In An Automated Microbial Detection System" by N. L. Fadler, et al; and U.S. design patent application Ser. No. 6,448 filed Jan. 25, 1979 entitled, "Biochemical Card For Use With An Automated Microbial Identification Machine" by Norman L. Fadler, et al. The information therein is incorporated by reference in this specification as though fully set forth herein below.

BACKGROUND OF THE INVENTION

The identification of the Enterobacteriacae family of bacteria is a common procedure in most medical microbiological laboratories. There are many products available which can be used to accomplish this task, i.e., the API, manufactured by Analytab Products; the R B System manufactured by Corning; the Enterotube manufactured by Roche Diagnostics and the Minitek manufactured by Baltimore Biologic Laboratories (BBL). These systems require a 24 to 48 hour incubation period and essentially are manual in nature. In such systems the unknown organism is introduced into a plurality of media which are later examined for evidence of sustenance of the microorganism by comparing the results of the plurality of tests with a matrix or formula. A determination as to which organism was present initially can be made on a statistical basis.

Since the prior art systems essentially are manual in nature, errors can be made both in determining which media sustain the unknown microorganism and through accidental introduction of other organisms during the handling process which skew the results to make the statistical basis inaccurate. Also, such systems are labor intensive because the many media must be read manually and the addition of indicator chemicals to allow such reading is a time consuming process.

Presently there are existing processes and apparatus for determining the presence, identity and quantity of microorganisms which involve placing the microorganisms into micro quantities of culture media, some of which will sustain specific microorganisms. The media are chemically organized so that the optical characteristics of each changes in a predetermined manner when the media are sustaining specific type or types of microorganisms.

A convenient way to perform these processes is through the use of a card or cassette constructed with a rigid body in the form of a plastic plate which includes viewing wells or chambers which pass through the plate. Each of the wells is connected to a predetermined liquid specimen supply port by means of channels cut in one side of the plate. Each port includes a septum constructed from suitable sealing compound which allows passage of a hollow needle when a liquid specimen is being introduced into the port.

The card is constructed by first forming the plastic plate, inserting the septum and then covering one side of the plate with optically transparent adhesive tape. Chosen biochemical media in liquid form are then placed in the proper wells and freeze dried. The opposite side of the plate is thereafter covered with another layer of optically transparent adhesive tape to form, in effect, a sealed chamber with at least one supply port, a plurality of wells and a piping system therebetween.

To introduce a specimen into the viewing wells, a vacuum is drawn through the specimen and a hypodermic needle inserted through the septum of the filling port so that the air in the sealed chamber is evacuated. The vacuum is removed and atmospheric pressure is used to force the diluted liquid specimen into the card. This causes both the wells and the adjacent branches to be full of liquid containing microorganisms. When no means are provided to prevent it, the microorganisms which are sustained by the media in the viewing wells tend to migrate with the reconstituted media through the branches to other wells. This is undesirable because it can cause erroneous results when the wells are read. This is very important in a matrix type speciation card where multiple organisms may be growing in the same well, each having different locomotion characteristics. Another problem results because some of the metabolic processes of the microbes produce gasses which form bubbles in the viewing wells. Overflow chambers are normally provided adjacent the wells to provide for some bubbles such as those resulting from the filling process and the metabolic bubbles. However, the metabolic bubbles tend to migrate in the heretofore fashioned cards so that they interfere with the optical reading thereof. Also, in a speciation card, it is desirable to change the environmental conditions such as the amount of oxygen in selected wells since some of the matrix tests are best done in an micro aerophilic rather than an aerobic environment.

SUMMARY OF THE INVENTION

The present improved card solves many of the problems discussed above by providing labyrinth channels of equal length connecting each of the wells to the filling branch network so that mobile organisms tend to be restricted in a similar manner no matter where they find a well having the proper nutrients and environment for their well being. The overflow chambers include a bubble trap so that the larger bubbles formed during the filling process are trapped therewithin to reduce the chances of interference with the optical reading of the card. Also, portions of the card are covered with multiple layers of adhesive tape so that some wells are covered by tape which enables more oxygen to pass therethrough than others.

It is therefore an object of the present invention to provide an improved card for use in an automated microbial detection system especially one designed to speciate microbes.

Another object is to provide a micro detection card having similar labyrinths adjacent each viewing well therein so that random locomotion by organisms is similarly restricted no matter where the organisms appear.

Another object is to provide an automated microbial detection system card having some wells that favor micro aerophilic reactions and others which favor aerobic ones.

Another object is to provide an improved overflow chamber for a viewing well in a automated microbial detection system card.

These and other objects and advantages of the present invention will become apparent to those skilled in the art after considering the following detailed specification which covers a preferred embodiment thereof in conjunction with the accompanying drawing.

BRIEF DESCRIPTION OF THE DRAWING

FIG. 1 is a top plan view of a microbial speciation card including the improvements of the present invention;

FIG. 2 is an enlarged cross-sectional view taken at line 2—2 of FIG. 1;

FIG. 3 is an enlarged plan view of the area encircled at 3—3 in FIG 1; and

FIG. 4 is an enlarged cross-sectional view taken at line 4—4 of FIG. 3.

DETAILED DESCRIPTION OF THE SHOWN EMBODIMENT

Referring to the drawing more particularly by reference numbers, number 10 in FIG. 1 designates an improved card used in a process for speciating microorganisms. The card 10 is rectangular in shape measuring about 2½ by 3½ inches and is about ⅜" thick. Cards of similar size but slightly different configuration are used for identification and enumerating tests, and antibiotic susceptibility test and identification and enumerating tests.

The card 10, includes a rigid transparent plate 12 which preferably is formed from a suitable plastic such as polystyrene and is the same size and shape as the card 10. The plate 12 has a plurality of viewing wells 14 which extend completely through the plate 12 from one major surface 15 to the other 16 (FIG. 4). Each viewing well 14 defines a predetermined volume which may be any desired volume depending upon the size of the card 10. In the usual case, whatever the desired volume, all of the viewing wells 14 are equal. For clarity only illustrative wells 14 are shown although such card as shown is designed to have 30 wells as is shown in U.S. design patent application Ser. No. 6,448.

Located adjacent to each well 14 is an overflow chamber 18. These chambers 18 extend completely through the plate 12 and open out of the two major surfaces 15 and 16 thereof. Each chamber 18 is connected to its viewing well 14 by passageways 20 and 22 which are stacked one on top of each other. The passageways 20 and 22 are separated by an interior wall 23 which extends from the viewing well 14 to the bubble chamber 18. The overflow chambers 18 assist in the complete filling of the wells 14 and in the prevention and elimination of bubbles therefrom as will be explained in detail hereinafter.

The plate 12 further includes separate serpentine filling channels 24 leading to the viewing wells 14 from the feeder channels 26, which in turn communicate with the filler port 28. The filling and feeder channels 24 and 26 are quite shallow with respect to the thickness of the plate 12 and open out of the major surface 15 thereof as shown for channel 24 in FIG. 4. The filling port 28 is relatively large and deep when compared to the filling and feeder channels 24 and 26 and the port 28 opens out of both surfaces 15 and 16 like the viewing wells 14.

A passageway 30 is provided from the edge 32 of the plate 12, which passageway 30 is clogged by means of a rubber septum 34 through which a hypodermic needle can be inserted.

The complete card 10 is manufactured by first forming the plate 12 by means of a suitable mold. The rubber septum 34 is formed by insertion in plastic form through the open end 36 of the passageway 30. The septum 34 forms a breachable entry to seal the channels 24 and 26 and the viewing wells 14 of the card 10 from the outside atmosphere once the card 10 is completed. An annular discontinuity 38 is formed along the passageway 30 which assists the septum 34 to remain within the passageway 30 when the hypodermic needle is inserted and removed therefrom. The septum 34 normally is constructed from a curable rubber compound which tends to remain in place once it cures. The normally used silicone rubber liberates acetic acid as it cures. To prevent undesired contamination, the card 10 is then stored at suitable curing conditions long enough for the silicone rubber to stop acetic acid outgasing.

Once the septum 34 has cured, a layer 40 of transparent tape is adhesively bonded to the surface 16 of the plate 12. The tape layer 40 seals what will become the bottom of the wells 14 as shown in FIG. 4. The card 10 is then oriented with respect to gravity so that the surface 16 is beneath the plate 12. Thereafter, suitable culture media in liquid form are inserted as desired in the viewing wells 14. Since it is undesirable that the media flow down the connecting filler and feeding channels 24 and 26 and thus mix, a discontinuity 42 is provided to interrupt any undesired flow. Although the discontinuity 42 tends to restrict any media in liquid form from flowing along the serpentine channels 24, the undesirable mixing is also prevented by the sequence of the filling process since the media is freeze dried before a tape layer 44 similar to tape layer 40 is adhesively attached to the surface 15 of the plate 12. The use of a channel 24 having a U-shaped cross-section as shown in FIG. 4, rather than one completely enclosed, assists in preventing capillary action from drawing the liquid media along the channel 24. The entry location 46 of the channel 24 into the well 14 is, of course, adjacent the upper surface 15 and the entry location 46 generally intercepts the curved side 48 of the viewing wells 14 which are oval shaped. The passageways 20 and 22 intersect the wells 14 at the opposite curved sides 50 thereof adjacent the tape layers 44 and 40 respectively.

When the card 10 is to be used, a hypodermic needle, not shown, is inserted through the septum 34. The hypodermic needle is connected to a supply of diluted liquid specimen containing the microbes whose species is unknown. A vacuum is then drawn through the specimen and the hypodermic needle to remove the major portion of the air in the port 28 the channels 24 and 26 and the viewing wells 14. When the vacuum is released the liquid specimen is forced into the port 28, the channels 26 and 24 and the viewing wells 14 atmospheric pressure. During this operation the overflow chambers 18 preferably are oriented upwardly with respect to gravity from the viewing wells 14 so that any residual air or bubbles tend to congregate therein. The bubbles tend to form a large bubble in the chamber 18 whose position is restricted by the intermediate wall 23 between the two pasageways 20 and 22. The surface tension of the bubble prevents the bubble from dislodging from the chamber 18 and migrating to the viewing well 14. The viewing well 14, being oval or racetrack shaped, tends to cause smooth mixing and rehydration of the dried media therewithin without the generation of undesired offensive bubbles. The spiral flowing action of the specimen tends to scrub the walls and cause any bubbles to travel to the overflow chambers 18 where they combine with the existing large bubble and are trapped therein. Since the pasageways 20 and 22 are adjacent the surfaces 15 and 16 of the plate 12 the small bubbles produced by the microbes as metabolic products can pass therethrough without restriction no matter which surface 15 or 16 is oriented upwardly during incubation of the card.

In a speciation system where many different types of microbes are being hunted simultaneously, it is desirable to have some test wells 14 which are more suitable for microaerophilic reactions. For that reason, a second transparent tape layer 52 and 54 is placed over a portion of the plate 12 so that some wells 14 and their connecting channels 24 and 26, and the filling port 28 are doubly covered. The second tape layers 52 and 54 substantially reduce the amount of oxygen that can pass through the tape layers into the doubly covered wells 14 and thus assist microaerophilic reactions. In some instances the second tape layers 52 and 54 may have the same oxygen transmission characteristics as the tape layers 40 and 44 and in other instances tape which provides a more complete barrier can be used.

Thus there has been shown and described an improved card for use in an automated microbial detection system especially when it is desired to speciate microbes, which fulfills all the objects and advantages sought therefor. Many changes, alterations, modifications, other uses and applications of the subject improved card will become apparent to those skilled in the art after considering this specification together with the accompanying drawing. All such changes, alterations and modifications which do not depart from the spirit and scope of the invention are deemed to be covered by the invention which is limited only by the claims which follow.

What is claimed is:

1. A card for use in detecting the presence of microorganisms in a specimen wherein the card has:
   first and second sides;
   detection wells for containing microbe supportive media passing from said first side to said second side therethrough;
   filling port means therein;
   filler passageways formed in said first side of said card connecting said filling port means to said detection wells;
   first and second layers of transparent adhesive tape positioned on said first and second sides of said card respectively to cover said detection wells and filler passageways, said transparent adhesive tape of said first and second layers having a predetermined gas permeability; and
   third and fourth layers of transparent adhesive tape positioned on portions of said first and second sides of said card to doubly cover selected wells to change the accessibility thereof to flow thereinto from the outside atmosphere, said transparent adhesive tape of said third and fourth layers having predetermined gas permeabilities.

2. The card defined in claim 1 wherein said filler passageways include branch passageways and serpentine passageways, each well having its own serpentine passageway of essentially the same length and shape with at least one discontinuity provided in said serpentine filler passageway adjacent said detection cell.

3. The card defined in claim 1 wherein each of said detection wells includes:
   a bubble chamber;
   a pair of passageways connecting said detection well to said bubble chamber, said passageways extending along the opposite sides of said card and being defined in part by said first and second layers; and
   a wall positioned between said passageways, and between said detection well and said bubble chamber for trapping bubbles within said bubble chamber.

4. The card as defined in claim 3 wherein said bubble chamber is generally cylindrical in shape and said wall positioned between said passageways includes a first end forming a portion of said bubble chamber.

5. The card defined in claim 4 wherein said wells are oval in shape having first and second ends, wherein said filler passageways include branch passageways and serpentine passageways of equal length, each well having its own similarly shaped serpentine passageway, and wherein said bubble chamber passageways connect to said wells at said first ends and said serpentine filler passageways intercept said second ends.

6. The card as defined in claim 5 wherein each of said wells is generally semi-cylindrical in shape at its first and second ends and said wall positioned between said bubble chamber passageways has a second end which forms a portion of said first semi-cylindrical end.

7. The card defined in claim 1 wherein said predetermined gas permeability of said third and fourth layers is no greater than said predetermined gas permeabilities of said first and second layers.

8. A card for use in detecting the presence of microorganisms in a specimen wherein the card has;
   first and second sides;
   detection wells for containing microbe supportive media passing from said first side to said second side therethrough;
   at least one filling port;
   filler passageways formed between said filling port and said detection wells; and
   first and second layers of transparent adhesive tape, each having a predetermined gas permeability positioned on said first and second sides of said card respectively to cover said detection wells and filler passageways, each of said detection wells including:
   a bubble chamber;
   a pair of passageways connecting said detection well to said bubble chamber, said passageways extending along the opposite sides of said card and being defined in part by said first and second layers of transparent adhesive tape; and
   a wall positioned between said passageways, and between said detection well and said bubble chamber for trapping bubbles within said bubble chamber.

9. The card as defined in claim 8 wherein said bubble chamber is generally cylindrical in shape and said wall positioned between said bubble chamber passageways includes a first end forming a portion of said bubble chamber whereby said first end traps bubbles forming and combining in said bubble chamber, in said bubble chamber.

10. The card defined in claim 9 wherein said wells are oval in shape having first and second ends, wherein said filler passageways include serpentine passageways of equal length and identical shape and branch passageways, said branch passageways connecting said filler port to said serpentine passageways, each well having its own serpentine passageway, and wherein said bubble chamber passageways connect to said wells at said first ends and said serpentine filler passageways intercept said second ends.

11. The card as defined in claim 10 wherein each of said wells is generally semi-cylindrical in shape at its first and second ends and said wall has a second end which forms a portion of said first semi-cylindrical end.

12. The card as defined in claim 11 including: third and fourth layers of transparent adhesive tape, each having a predetermined gas permeability and being positioned on portions only of said first and second sides of said card to doubly double cover selected wells to change the accessibility thereof to the outside atmosphere so that said doubly covered wells are thereby adapted to encourage microaerophilic reactions.

13. The card defined in claim 12 wherein said predetermined gas permeability of said third and fourth layers of transparent adhesive tape is no greater than said predetermined gas permeabilities of said first and second layers.

* * * * *